United States Patent [19]

Johnson, Jr.

[11] 4,059,620

[45] Nov. 22, 1977

[54] PROCESS FOR PREPARING OLEFIN SULFONATES

[75] Inventor: Fred Lowery Johnson, Jr., Austin, Tex.

[73] Assignee: Texaco Development Corporation, New York, N.Y.

[21] Appl. No.: 361,264

[22] Filed: May 17, 1973

[51] Int. Cl.$^2$ .......................................... C07C 139/00
[52] U.S. Cl. .............................. 260/513 T; 260/456 R
[58] Field of Search .............. 260/456 R, 457, 513 R, 260/513 T

[56] References Cited

U.S. PATENT DOCUMENTS

| | | | |
|---|---|---|---|
| 3,328,460 | 6/1967 | Vander Mey | 260/513 R |
| 3,350,428 | 10/1967 | Brooks et al. | 260/456 R |
| 3,427,342 | 2/1969 | Brooks et al. | 260/457 |
| 3,441,191 | 5/1969 | Nielsen | 260/513 R |
| 3,531,518 | 9/1970 | Ohren et al. | 260/513 R |
| 3,769,332 | 10/1973 | Nagayama et al. | 260/513 R |
| 3,781,339 | 12/1973 | Tuvell et al. | 260/513 R |

*Primary Examiner*—Norman Morgenstern
*Attorney, Agent, or Firm*—James L. Bailey

[57] ABSTRACT

An improved process for preparing olefin sulfonic acids and sulfonates by the reaction of sulfur trioxide and an olefin mixture having 14 to 16 carbon atoms per molecule which includes at least 30 percent by weight dimer olefins is disclosed. The olefin mixture and sulfur trioxide are mixed and reacted in a reaction zone of a continuous falling film reactor apparatus having a segregated cooling jacket, wherein the upper ⅓ to ⅔ of the reaction zone is operated and maintained at a constant temperature of between about 0° to below about 27° C and the lower ⅓ to ⅔ of the reaction zone is operated and maintained at a higher constant temperature of between about 25° to about 40° C. The acidic reactor effluent is then aged prior to neutralization. The improved process produces a resulting product having a low oil content and low color at increased production rates while greatly reducing the off gas plume for improved air pollution abatement.

7 Claims, No Drawings

PROCESS FOR PREPARING OLEFIN SULFONATES

BACKGROUND OF THE INVENTION

1. Field of the Invention

The invention relates to the preparation of olefin sulfonates and more particularly pertains to an improved process for producing olefin sulfonic acids and sulfonates of improved low oil content and low color from mixtures of olefins having 14 to 16 carbon atoms per molecule which contain at least 30 percent by weight dimer olefins.

2. Description of the Prior Art

Processes for producing olefin sulfonic acids and olefin sulfonates by the use of continuous falling film reactor apparatus are well known in the art. Generally, conventional continuous falling film reactor apparatus comprise a vertical reaction zone surrounded by a suitable heat exchange means, and include means for forming a continuous falling thin film of olefin product in the reaction zone and a means for injecting sulfur trioxide into the reaction zone. The thin continuous falling film of the olefin to be sulfonated is formed in the reaction zone and sulfur trioxide, with a gaseous diluent, is mixed and reacted therewith. The sulfonation reaction which occurs is normally highly exothermic, depending upon the particular olefin utilized, resulting in an olefin sulfonic acid reaction product or effluent. Through the use of the heat exchange means, the exothermic reaction temperature can be substantially controlled, thereby retarding degradation of the acidic reaction product which produces off-color and other undesirable problems. Examples of prior art processes for preparing olefin sulfonates by the use of continuous falling film reactor apparatus are disclosed in the following U.S. Pat. Nos.: 3,169,142; 3,501,276; 3,420,875; and 3,461,053.

There are, of course, several variations known in the art of the above-described somewhat conventional process and apparatus for the production of olefin sulfonic acids and sulfonates. For instance, Brooks teaches in U.S. Pat. No. 3,620,684 an improved process and apparatus for continuous sulfonation of olefins wherein the acidic reaction product of an olefin and sulfur trioxide mixed and reacted in a reaction zone is immediately cooled after passing from the reaction zone, to retard degradation thereof. The preferred method of cooling disclosed is a recycle-quench step of the acidic reaction product which aids completion of the sulfonation reaction.

However, attempts heretofore to produce olefin sulfonic acids and sulfonates of low oil content and low color from olefin feed mixtures having 14 to 16 carbon atoms per molecule wherein at least 30 percent by weight of the mixtures are dimer olefins have been substantially unsuccessful, particularly at acceptable production rates. The acidic reaction products or effluent from the above-described $C_{14}$-$C_{16}$ dimer olefin mixtures mixed and reacted with sulfur trioxide are highly thermally sensitive. On the other hand, the sulfonic acid and sulfonate products prepared from $C_{14}$-$C_{16}$ dimer olefin mixtures are highly desirable for use in preparing light duty liquid detergents which are biodegradable. In the preparation of these products by prior art processes, the production rate is normally quite low and additional treatment steps are usually required to lower the oil content and off-color.

Another disadvantage in the use of known prior art processes and apparatus for preparing olefin sulfonic acids and sulfonates from the above-described $C_{14}$-$C_{16}$ dimer olefin mixtures is the concurrent production of off gas plumes that are most difficult to treat for air pollution abatement. Tests have shown that these off gas plumes include not only inert diluent gas and unreacted sulfur trioxide but also large amounts of the sulfonic acid reaction product in aerosol form. Hence, expensive pollution abatement devices must be utilized, e.g., alkaline scrubbing devices, after burners and the like, before the off gas plume can be released into the atmosphere.

SUMMARY OF THE INVENTION

The present invention is an improved process for preparing olefin sulfonic acids and sulfonates by the reaction of sulfur trioxide and an olefin in the reaction zone of a continuous falling film reactor apparatus to produce an acid reaction effluent followed by aging and neutralization. The improvement of the invention comprises mixing and reacting sulfur trioxide and a mixture of olefins containing 14 to 16 carbon atoms per molecule, wherein at least 30 percent by weight of the mixture is dimer olefins, in the reaction zone of a continuous falling film reactor apparatus, operating and maintaining the upper $\frac{1}{8}$ to $\frac{1}{3}$ of the reaction zone at a constant temperature of between about 0° to below about 27° C, operating and maintaining the lower to $\frac{2}{3}$ of the reaction zone at a higher constant temperature of between about 25° to 40° C and then aging the resultant acidic reactor effluent at about 20°-45° C prior to neutralization. By the practice of the invention, the resultant acidic reaction product and/or sulfonate product, produced after conventional neutralization, have low oil content and low color, even when produced at high production rates. The resultant products are highly acceptable for use in the production of biodegradable, light-duty liquid detergents. Moreover, by the practice of the invention, the off gas plume contains greatly reduced levels of aerosol acidic product along with an improvement in product recovery.

Other objects and advantages of this invention will become readily apparent to one skilled in the art from the ensuing descriptions of the invention.

DETAILED DESCRIPTION OF THE PREFERRED EMBODIMENTS

As mentioned hereinbefore, the instant invention is applicable for the preparation of olefin sulfonic acids and sulfonates from mixtures of olefins having 14 to 16 carbon atoms per molecule that contain at least 30 percent by weight dimer olefins. The remaining 70 percent by weight of the mixtures may be $C_{14}$-$C_{16}$ alpha olefins. However, it will be readily understood by those skilled in the art that the applicable olefin mixtures may contain minimal amounts of alpha, and/or dimer olefins having from 12 to 20 carbon atoms per molecule and internal olefins along with certain unknowns or impurities, e.g., below about 10 percent by weight of the olefin feed mixture.

The invention is especially applicable for the preparation of olefin sulfonic acids and sulfonates from $C_{14}$-$C_{16}$ olefin feed mixtures containing about 30–70 based upon the weight of the total mixture, with 50% by weight dimer being optimum. In addition, a preferred olefin feed mixture has an average molecular weight of about 196 to 224. The resulting products are highly desirable for the preparation of biodegradable light duty liquid detergents.

In carrying out the instant invention, a continuous falling thin film of the above-described olefin mixture is formed in a reaction zone of a continuous falling film reactor apparatus. Sulfur trioxide is then mixed and reacted therewith in a conventional manner, such as by injection a sulfur trioxide vapor, with a diluent inert gas, into the reaction zone under pressure to increase turbulence in the falling film of olefin mixture. Procedures and apparatus for forming thin films of an olefin mixture and mixing and reacting them with sulfur trioxide in a reaction zone are well known in the art, as mentioned hereinbefore and, hence, a detailed description thereof will not be set forth.

However, in the present invention, the upper ⅛ to ⅓ of the reaction zone of the apparatus is operated and maintained at a constant temperature of between about 0° to below about 27° C while the olefin film and fulfur trioxide are mixed and reacted. Although any conventional means known in the art for maintaining a constant temperature may be used, we prefer to surround the reaction zone with a segregated cooling jacket and circulate through the upper section thereof a heat absorbing fluid, e.g., water, that will remove exothermic reaction heat from the reaction zone at an adequate rate to maintain constancy.

It has been shown that the exothermic reaction of the olefin mixture and sulfur trioxide is very rapid and approaches completion while the falling film of olefin and reaction product is within the upper ⅛ to ⅓ of the reaction zone. Accordingly, I have found that by operating and maintaining the upper ⅛ to ⅓ of the reaction at a constant temperature between 0° to below about 27° C a superior sulfonic acid product and superior sulfonate product, after neutralization, is obtained with excellent low oil content and low color characteristics, yet the rate of production can be increased greatly. Moreover, most unexpectedly there is a great reduction in off gas plume containing the sulfonic acid reaction product in aerosol form which tremendously facilitates pollution abatement.

Furthermore, experiments have shown that maintaining and operating the upper ⅛ to 166 of the reaction zone at the above-described temperature range is most critical. I have found that when the upper level is operated and maintained at constant temperatures either below 0° or above about 27° C, even at conventional production rates, the resulting acidic reaction effluent after neutralization contains unacceptably high levels of oil and exhibits high off-color.

The lower ⅞ to ⅔ of the reaction zone of the apparatus is then operated and maintained at a higher constant temperature of between about 25° C to 40° C by any conventional means, e.g., circulating a heat absorbing fluid through a segregated cooling jacket surrounding the reaction zone. It is most critical to operate and maintain the lower part of the reaction zone at a higher constant temperature within this range in order to accomplish the desired objectives. The viscosity of the mixture of unreacted olefin and acidic reaction product formed in the reaction zone increases proportionately as the reaction between the olefin and sulfur trioxide approaches completion. As viscosity increases the rate of film flow decreases, thereby increasing the exposure of the acidic reaction product to exothermic reaction temperatures which results in thermal degradation of the reaction product. As mentioned hereinbefore, sulfonic acids produced from $C_{14}$-$C_{16}$ olefin mixtures containing at least 30 percent by weight dimer olefin are highly thermally sensitive. This thermal sensitivity increases proportionately with the amount of dimer olefin.

Moreover, experiments have shown that as the percent by weight ratio of alpha olefin in the olefin feed mixture increases, the above-described segments of the reaction zone must be operated at proportionally higher temperatures, within the stated ranges. Accordingly, as the ratio of dimer to alpha olefin in the feed mixture increases, proportionally lower temperatures within the stated ranges can be employed. The optimum temperatures to be used in the operation of each segment of the reaction zone is thus dependent upon the particular make-up of the olefin feed mixture and is best determined empirically.

Although the above-described olefin feed mixture may be fed to the reaction zone of the continuous falling film reactor apparatus at any desired temperature that will permit the formation of a continuous falling thin film of olefin in the reaction zone, a temperature of between about 20°-25° C is preferred. Optimally, the olefin feed mixture is fed to the reaction zone at room temperature. Accordingly, the temperature of the sulfur trioxide is preferably between about 30°-35° C when it is injected into the reaction zone. In a preferred embodiment of the invention, a $C_{14}$-$C_{16}$ olefin feed mixture containing 30 to 70 percent by weight dimer olefin is mixed and reacted with $SO_3$ vapor in a reaction zone wherein the upper ¼ of the reaction zone is operated and maintained at a constant temperature of between about 0°-10° C. The lower ¾ of the reaction zone is operated and maintained at a higher constant temperature of between about 25°-30° C. The upper and lower parts of the reaction zone are maintained at the designated constant temperature ranges by the use of a segregated cooling jacket surrounding the reaction zone.

The acidic reaction effluent is then aged at a temperature of between about 20°-45° C. Preferably, the effluent is aged for about 1-10 minutes at approximately room temperature. Although the aging step may be performed by the use of any conventional means, I prefer to pass the reactor effluent from the reaction zone to a cyclone phase separator. During aging, any unreacted olefin mixture remaining in the effluent is placed in further contact with sulfur trioxide for reaction and the temperature of the acidic reaction effluent is stabilized. More importantly, the aging provides the opportunity for isomerization of certain sultone structures in the acidic reactor effluent. Specifically, the aging time prevents formation of highly insoluble betahydroxy sulfonates in the final neutralized and hydrolyzed product.

The aged acidic reaction effluent is then neutralized by any conventional procedure, e.g., by mixing and reacting the effluent with a caustic solution, which produces the olefin sulfonate product. The resultant neutralized olefin sulfonate product can then be further treated by any of the processes known in the art such as by hydrolysis (saponification) to provide products ready for use.

Through the practice of the instant invention, $C_{14}$-$C_{16}$ olefin sulfonates containing at least 30 percent by weight dimer olefins can be produced that have below about 5.0 percent oil content (basis solids) and exhibit a Klett color below about 150 (unbleached, as determined with a Klett colorimeter with a No. 42 blue filter with a 40 mm cell on a 5% solid solution in water)

even at increased production rates up to about 23 lb/ft²/hr (pounds feed olefin +SO₃ per square foot reactor surface per hour).

As mentioned hereinbefore, any conventional continuous filling film reactor apparatus may be utilized in the practice of the invention so long as the apparatus is capable of being operated and maintained at a temperature of between about 0° to below about 27° C in the upper ⅛ - ⅓ of the reaction zone and at a temperature of between about 25° - 40° C at the lower ⅞ - ⅔ of said reaction zone. Accordingly, sulfur trioxide may be obtained from any conventional source. We prefer to utilize SO₃ vapor from liquid SO₃, mixed with an inert gaseous diluent, e.g., air, nitrogen, carbon monoxide, carbon dioxide, sulfur dioxide and the like. The gaseous SO₃ is preferably utilized in a concentration from about 1.0 volume percent to 10 percent in the gas feed. Moreover, the mole ratio is preferably between about 1.05 to 1.20 (SO₃:olefin).

In the following examples a continuous falling film reactor apparatus consisting of three or four sections, each with its own water cooling jacket and connected together with ball joints was utilized. The reaction zone of the apparatus was defined by a reactor tube that was 5 mm (0.197 inches) I.D., constructed of glass and had a length:diameter ratio (L/D) of 165 for three sections or 234 for four sections. An olefin reservoir near the top surrounded the reactor tube and the olefin mixture being mixed and reacted overflowed a cut in the reactor tube to flow down the reactor inner wall in a thin film. SO₃ vapor, from SO₃ originally pumped as a liquid into a heated bomb swept with dry air, emerged into the reactor tube at a point below the top of the upper water jacket where it contacted the olefin mixture film as it moved downwardly the reactor wall. Adequate turbulence in the olefin film was generated by the SO₃-air stream plus a secondary air stream entering the reactor tube from above the olefin mixture feed point. Air fed through the reaction zone was dried over 3-A molecular sieves and metered by rotameters. The olefin feed mixture was pumped with a microbellows metering pump, and the liquid SO₃ was pumped either with a syringe pump or a Ruska pump for larger feed rates. Water was pumped through the reactor cooling jackets at 0.3 - 0.7 g.p.m. to provide the desired constant temperatures on the reactor tube wall. In all the following Examples except Example 1, the acidic reaction effluent was passed through a cyclone phaseseparator which was cooled to the same temperature as the lower part of the reactor. The liquid effluent was then passed through an ager (a vessel to hold the liquid for a predetermined length of time) at room temperature and thence into a caustic solution for neutralization. In Example 1, a less efficient glass cyclone was used as a phase separator and the liquid effluent was collected as acid, aged at least 10 minutes after the run, then neutralized with caustic. In all the Examples, the neutralized slurry was saponified in a pressure bottle in a 150° C oven for 1 to 1½ hours.

The saponified slurry was then analyzed for unsulfonated oil by extraction with pentane, evaporation of the pentane and weighing the oil. Color was determined with a Klett colorimeter with a No. 42 blue filter and a 40 mm cell on a 5 percent solids solution in water.

Also, in the following examples production rate is defined by pounds feed (olefin + SO₃) per square foot reactor wall surface per hour (lb/ft²/hr). When the reaction zone L/D is 234, the surface is 0.198 ft². When the reaction zone L/D is 165, surface area is 0.146 ft².

Reactor linear velocity is defined as the velocity of the air feed through the reactor tube in ft/sec. SO₃ concentration is defined as the volume percent SO₃ in the total gas feed. Mole ratio is defined as moles SO₃ fed per mole olefin mixture fed. The examples are for purposes of illustration of our invention and are not intended to be limiting thereof.

EXAMPLES 1-2

Examples 1 and 2 set forth in the following Table I illustrate the advantage of mixing and reacting SO₃ and an all dimer $C_{14}$-$C_{16}$ olefin blend in a reactor with the upper part of the reactor cooled to near 0° C and the lower part of the reactor operated and maintained at a constant temperature of near 25° C. The olefin feed in both examples consisted of 70 percent $C_{14}$ dimer and 30 percent $C_{16}$ dimer with an average molecular weight of 204.

TABLE I

| | Example No. 1 | Example No. 2 |
|---|---|---|
| Production Rate (lb/ft²/hr) | 6.4 | 6.4 |
| Mole Ratio | 1.15 | 1.16 |
| SO₃ Concentration in Gas Feed (%) | 2 | 2 |
| Reactor Linear Velocity (ft/sec.) | 125 | 125 |
| Reactor L/D | 234 | 234 |
| Reactor Cooling Jacket Temperatures | | |
| (° C) upper ⅓ | 1-4 | 51 |
| lower ⅔ | 27 | 51 |
| % oil (basis solids) | 3.7 | 14.1 |
| Klett Color | 71 | 570 |

EXAMPLES 3-7

The following Table II shows the effect on oil and color of operating and maintaining the reaction zone with the top too cold (Example 3), and with the top at 0, 10, 25, and 40° C, all with the lower part of the reaction zone operated and maintained at a temperature warm enough to permit rapid flow of the acidic reaction effluent from the reaction zone (25° C). Example 4, wherein the upper ⅓ of the reaction was operated and maintained at 0° C and the lower ⅔ was operated and maintained at 25° C, gave the best results on oil and color considered together. The olefin feed mixture used in Examples 3-7 consisted of 27.6 percent alpha olefin, 63.4 percent vinylidene olefin, 7.2 percent internal olefin, 1.1 percent paraffin and 0.07 percent unknown, based upon the weight of the olefin feed mixture. The carbon distribution of the feed mixture was 0.3 percent $C_{12}$, 69.1 percent $C_{14}$ and 30.4 percent $C_{16}$ with an average molecular weight of 205.

TABLE II

| Example No. | 3 | 4 | 5 | 6 | 7 |
|---|---|---|---|---|---|
| Production Rate (lb/ft²/hr) | 9.8 | 9.8 | 9.8 | 9.8 | 9.8 |
| Mole Ratio | 1.08 | 1.08 | 1.08 | 1.08 | 1.08 |
| SO₃ Concentration (%) | 2.2 | 2.2 | 2.2 | 2.2 | 2.2 |
| Linear Velocity (ft/sec) | 125 | 125 | 125 | 125 | 125 |
| Reactor L/D | 165 | 165 | 165 | 165 | 165 |
| Jacket Temp. (° C) | | | | | |
| Upper ⅓ | −10 | 0 | 10 | 25 | 40 |
| Lower ⅔ | 25 | 25 | 25 | 25 | 25 |
| Oil (Basis Solids) (%) | 3.5 | 3.6 | 3.8 | 5.1 | 5.2 |
| Klett Color | 144 | 75 | 88 | 87 | 86 |

EXAMPLES 8-10

In the following Table III, Examples 8-10 illustrate that lower oil content can be obtained at high production rates by the practice of the instant invention than at lower production rates using higher temperatures in the upper part of the reaction zone. The same feed was used as in Examples 3-7.

TABLE III

| Example No. | 8 | 9 | 10 |
|---|---|---|---|
| Production Rate (lb/ft²/hr) | 23.4 | 15.7 | 9.8 |
| Mole Ratio | 1.08 | 1.07 | 1.08 |
| SO₃ Concentration (%) | 2.2 | 2.2 | 2.2 |
| Linear Velocity (ft/sec) | 125 | 125 | 125 |
| Reactor L/D | 165 | 165 | 165 |
| Jacket Temp (° C) | | | |
| upper ⅓ | 0 | 0 | 25 |
| lower ⅔ | 25 | 25 | 25 |
| % Oil (B/S) | 4.8 | 3.7 | 5.1 |
| Klett Color | 135 | 82 | 87 |

EXAMPLES 11-13

Table IV shows the off-gas plume reduction achieved by operating and maintaining the upper ⅓ of the reaction zone at a constant lower temperature and by operating and maintaining the lower ⅔ of the reaction zone at a higher constant temperature. The reduction is shown as a reduced loss of product (increased percent recovery of feeds on material balance) because no numerical data are available for the visual density of the plume. The same olefin feed mixture was used in the Examples of Table IV as in Examples 3-10.

TABLE IV

| Example No. | 11 | 12 | 13 |
|---|---|---|---|
| Production Rate (lb/ft²/hr) | 9.8 | 9.8 | 9.8 |
| Mole Ratio | 1.08 | 1.08 | 1.08 |
| SO₃ Concentration (%) | 2.2 | 2.2 | 2.2 |
| Linear Velocity (ft/sec) | 125 | 125 | 125 |
| Reactor L/D | 165 | 165 | 165 |
| Jacket Temp. (° C) | | | |
| Upper ⅓ | 0 | 40 | 40 |
| Lower ⅔ | 25 | 25 | 40 |
| Loss of Product in Plume (%) | 4.2 | 6.0 | 8.2 |
| Reduction of Loss in Plume (%) | 42.8 | 26.8 | — |

EXAMPLES 14-16

The following Table VI illustrates the optimum results obtained when the upper 25% of the reaction zone is operated and maintained at a temperature within the prescribed range and the lower 75% of the reaction zone is operated and maintained at a higher constant temperature. In Examples 14 and 15, the olefin feed mixture consisted of 28% $C_{14}$ alpha, 40% $C_{14}$ dimer and 29% $C_{16}$ dimer, by weight. The olefin feed mixture of Example 16 consisted of 57% $C_{14}$ dimer and 42% $C_{16}$ dimer, by weight.

TABLE V

| Example No. | 14 | 15 | 16 |
|---|---|---|---|
| Production Rate (lb/ft²/hr) | 7.1 | 7.1 | 9.8 |
| Mole Ratio | 1.11 | 1.11 | 1.08 |
| SO₃ Concentration (%) | 2.0 | 2.0 | 2.2 |
| Linear Velocity (ft/sec) | 125 | 125 | 125 |
| Reactor L/D | 234 | 234 | 165 |
| Reactor Cooling Water (° C) | | | |
| Upper ¼ | 2-4 | 38 | 1-2 |
| Lower ¾ | 38 | 38 | 25.6 |
| % Oil (Basis Solids) | 2.1 | 4.2 | 4.1 |
| Klett Color | 161 | 182 | 120 |

A comparison of Examples 14 and 15 show that cooling the upper 25% of the reaction zone improves oil content of the resultant product 100% even when the lower ¾ of the reaction zone is operated and maintained at the same constant temperature. In addition, it is pointed out that the run of Example 15 produced a very dense off-gas plume containing a high level of the sulfonic acid product in aerosol form.

Obviously, many modifications and variations of the invention as hereinbefore set forth may be made without departing from the spirit and scope thereof, and, therefore, only such limitations should be imposed as are indicated in the appended claims.

I claim:

1. In the process for preparing olefin sulfonates by the reaction of sulfur trioxide and an olefin feed mixture in a continuous falling film reactor apparatus to produce an acid reaction effluent followed by aging and neutralization to convert said effluent to an olefin sulfonate, wherein the improvement comprises:

mixing and reacting a mixture of olefins having 14 to 16 carbon atoms per molecule, at least 30 percent by weight to 70 percent by weight of said olefin mixture being dimer olefins, and sulfur trioxide in a reaction zone of a continuous falling film reactor apparatus;

operating and maintaining the upper ⅛ to ⅓ of the reaction zone at a constant temperature of between about 0° C. to below about 10° C.;

operating and maintaining the lower ⅞ to ⅔ of said reaction zone at a higher constant temperature of between about 25° C. to about 40° C.; and aging the resultant acidic reaction effluent at a temperature of about 20°-45° C. prior to neutralization.

2. The process according to claim 1, wherein the olefin mixture is 50 percent by weight dimer olefin.

3. The process according to claim 1, wherein the upper ¼ of said reaction zone is operated and maintained at a constant temperature of between about 0° C to below about 10° C and the lower ¾ of said reaction zone is operated and maintained at a higher temperature of between about 25° C to about 40° C.

4. The process according to claim 1, wherein the olefin feed mixture has an average molecular weight of between about 196 to about 224.

5. The process according to claim 1, wherein said resultant acidic reactor effluent is aged at about 20°-35° C for about 1-10 minutes prior to neutralization.

6. The process according to claim 1, wherein said olefin mixture contains 50 percent by weight dimer olefin having an average molecular weight of between about 196 to 224, the upper ¼ of the reaction zone is operated and maintained at a constant temperature of about 0° to 10° and the lower ¾ of said reaction zone is operated and maintained at a higher constant temperature of about 25° to 40° C.

7. The process according to claim 1, wherein the upper ⅛ to ⅓ of the reaction zone is operated and maintained at said constant temperature and the lower ⅞ to ⅔ of the reaction zone is operated and maintained at said higher constant temperature by the use of segregated water cooling jacket surrounding said reaction zone.

* * * * *